United States Patent [19]

Miklas

[11] 3,937,748
[45] Feb. 10, 1976

[54] OXIDATIVE DEHYDROGENATION USING GEL PRECIPITATED CATALYST PREPARATION

[75] Inventor: Edward J. Miklas, Conroe, Tex.

[73] Assignee: Petro-Tex Chemical Corporation, Houston, Tex.

[22] Filed: Aug. 26, 1974

[21] Appl. No.: 500,243

Related U.S. Application Data

[60] Division of Ser. No. 365,916, June 1, 1973, Pat. No. 3,849,545, which is a continuation-in-part of Ser. No. 122,162, March 8, 1971, abandoned.

[52] U.S. Cl. ....... 260/680 E; 260/669 R; 260/683.3; 260/696
[51] Int. Cl.² ........................................... C07C 5/48
[58] Field of Search ..................... 260/680 E, 669 R

[56] References Cited
UNITED STATES PATENTS

| | | | |
|---|---|---|---|
| 3,303,235 | 2/1967 | Croce et al. | 260/680 E |
| 3,334,152 | 8/1967 | Bavars et al. | 260/680 E |
| 3,843,745 | 10/1974 | Christman et al. | 260/680 E |
| 3,849,545 | 11/1974 | Miklas | 260/680 E |

Primary Examiner—Paul M. Coughlan, Jr.
Attorney, Agent, or Firm—Elton N. Dry; Kenneth H. Johnson

[57] ABSTRACT

Improved zinc ferrite oxidative dehydrogenation catalyst can be prepared by co-precipitating the catalysts from a solution of zinc and iron ions in the presence of a high molecular weight polyhydric material such as dextran in a 2 to 4 normal alkali metal hydroxide solution. The result of having the polyhydric material present is that the precipitate has the form of a granular gelatinous precipitate of improved processability. The catalyst itself is more active in dehydrogenations and physically stronger than comparable catalyst prepared by conventional methods. More importantly, zinc ferrite catalysts prepared in this manner have extremely long useful lives whereas those prepared by conventional methods have very short useful lives.

18 Claims, No Drawings

OXIDATIVE DEHYDROGENATION USING GEL PRECIPITATED CATALYST PREPARATION

This application is a division of Ser. No. 365,916, filed June 1, 1973, now U.S. Pat. 3,849,545, which was a continuation-in-part of Ser. No. 122,162, filed Mar. 8, 1971, and now abandoned.

The present invention relates to a zinc ferrite oxidative dehydrogenation catalyst more particularly the invention relates to a method for preparing the zinc ferrite catalyst and the method of using the zinc ferrite catalyst.

The types of dehydrogenation catalysts known are quite varied. Generally dehydrogenation catalysts comprise a metal compound or mixture of metal compounds. Such compounds include the metal oxides, metal salts such as the halides, phosphates, sulfates, molybdates, tungstates, and the like. Generally, these catalysts can be characterized as compounds containing a metal having a polyoxidation state, i.e., a metal having at least two oxidation states, in addition to the zero state. Suitable metals are found in Groups IVB, VB, VIB, VIIB, VIII, IB, IVA, VA and VIA of the Periodic Table* of elements. Particularly useful polyoxidation state metals are Ti, V, Cr, Mn, Fe, Co, Ni, Cu, Nb, Mo, Ru, Rh, Pd, Sn, Sb, W, Re, Os, Ir, Pt, Au, Hg, Tl, Pb, Bi and Po.

*Handbook of Chemistry and Physics, 45th Ed., 1964–1965. The Chemical Rubber Co., Cleveland, Ohio, p.B-2.

Among the preferred catalysts of this type are those which contain iron, oxygen and at least one other metallic element Me. The catalysts are often termed ferrites. Ordinarily the ionic radius of the second metallic ingredient(s) Me is small enough that the oxygen anions are not spread too far apart. That is, the elements must be able to form a crystalline structure with the iron and oxygen.

A preferred ferrite catalyst is that having a face-centered cubic form of crystalline structure. Examples of this type of catalyst are ferrites of the general formula $MeO.Fe_2O_3$ where Me is a divalent metal cation such as $Mg^{--}$ $Ni^{--}$ or $Zn^{--}$. However, the spinel structure may not occur and other types of ferrites having a hexagonal crystal may be formed. The hexaggonal ferrites are within the scope of the definition of catalysts of this invention. Examples of ferrite catalysts are such as magnesium ferrite, cobalt ferrite, nickel ferrite, zinc ferrite, barium ferrite, strontium ferrite, manganese ferrite, calcium ferrite, cadmium ferrite, silver ferrite, zirconium ferrite, and rare earth ferrites such as cerium ferrite or mixtures of ferrites, such as ferrites containing iron combined with at least one element selected from the group consisting of Mg, Zn, Ni, Co, Mn, Cu, Cd, Ca, Ba, Sr, Al, Cr, Ti, V, Mo, W, Na, Li, K, Sn, Pb, Sb, Bi, Ga, Ce, La, Th, Pr, Nd, Pm, Sm, Eu, Gd, Tb, Dy, Ho, Er, Tm, Yb, Lu and mixtures thereof with a preferred group being Mg, Ca, Sr, Ba, Mn, Cr, Co, Ni, Zn, Cd and mixtures thereof. A number of such catalyst are described in the following U.S. Pat: Nos. 3,420,911; 3,420,912; 3,428,703; 3,440,299; 3,260,767; 3,274,285; 3,284,536; 3,303,234-7; 3,320,329; 3,334,152, 3,336,408; 3,342,890; 3,404,193; 3,437,703; 3,446,869; 3,456,030.

It is an object of this invention to provide a process for producing a zinc ferrite oxidative dehydrogenation catalyst with a long useful life. It is a further object of this invention to provide a process of catalyst preparation that is easily carried out. It is a further object to provide a catalyst which will have long catalytic life and exhibit excellent physical strength. It is another object of this invention to provide an oxidative dehydrogenation catalyst which will give high yields of the desired dehydrogenation products. These and other objects and advantages of the present invention will become apparent from the following description of the invention.

SUMMARY OF THE INVENTION

The present invention provides a method of preparing zinc ferrite dehydrogenation catalysts which have the intimate contact desirable and possible from the precipitation methods of preparation and yet have physical strength superior to the precipitated catalyst.

In the case of the zinc ferrite oxidative dehydrogenation catalyst several other improvements are obtained by the present invention including the use of higher oxygen to hydrocarbon ratios without substantial loss of selectivity thus higher yields, lower inlet temperatures, and longer catalyst life than analogous but conventionally prepared catalysts, under similar operating conditions.

Another advantage found with the present catalyst is the increased control of the reaction. Oxidative dehydrogenation reactions are exothermic thus some means must be employed to control the temperature. Two particular means are heat exchangers for heat removal or a diluent, such as steam, in the feed stream. In either case the instant catalyst provides greater control, but in the adibatic process it has been found that the quantity of steam diluent can be reduced from that normally required thus effecting a substantial utility savings.

Briefly stated, one aspect of the present invention is an improvement in the method of preparing a zinc ferrite oxidative dehydrogenation catalyst comprising contacting a solution of a soluble metal component comprising zinc and iron with a precipitating agent to precipitate an insoluble metal component comprising zinc and iron in the presence of a high molecular weight soluble polyhydric organic compound and calcining the precipitate wherein the improvement comprises employing as the precipitating agent solution of a hydroxide of a metal selected from the group consisting of Li, Na, K, Rb and Cs, said precipitating solution having a normality of between 2 and 4. As used herein and in the claims the term "metal component" is understood to mean zinc and iron alone or in admixture with other metal compounds having the same or different anions and/or cations. The term "normality" is used in its usual and conventional meaning and is understood to mean the gram equivalents of the dissolved substance per liter, i.e., the gram molecular weight of the dissolved substance divided by the hydrogen equivalent of the substance per liter of solution.

The mechanism of the polyhydric material is not fully understood. It is possible for some polyhydric compounds to form complexes with metals, however, this does not appear to be essential to the present invention. The high molecular weight of the polyhydric material imparts polymeric qualities of viscosity and surface tension to the solution. The term polyhydric is used to describe a material having at least two and preferably three or more hydroxyl groups or groups that produce hydroxyl groups under conditions of the preparation. The term high molecular weight is used to mean a material having a molecular weight of at least about 3000 (number average) or more. The term soluble is used to indicate that the polyhydric material is sufficiently soluble to give the improved catalyst. It is also generally expected that the precipitating medium will be aqueous, however, it is contemplated that other solvents can be employed within the scope of this invention.

The molecular weight of the soluble polyhydric organic compounds is not critical, but it should be appreciated that lower molecular weights than about 3000 may not provide a satisfactory environment for the formation of the gel. Generally the molecular weight will be at least 4000 with the upper limit being set by solubility consideration and also the viscosity of the precipitating medium. Since the precipitating agent must contact the metal ions, the viscosity of the precipitating medium cannot be too great. Generally, soluble polyhydric materials that will allow mixing of the metal ions and precipitating agent will not have molecular weights of greater than 400,000.

The polyhydric organic compounds contemplated include polyhydric alcohols, including polyesters such as those derived from polybasic acids as adipic, succinic, sebacic, azelaic and phthalic polyols as pentaerythritol, xylitol and sorbitol, polyethers such as the condensation products of ethylene oxide, propylene oxide and mixtures thereof with polyols such as glycerol, pentaerythritol, xylitol, sorbitol and polysaccharides, and hydrolyzed polymers such as polyvinyl acetate to polyvinyl alcohol. The polyesters and polyethers are widely known and commercially used in the preparation of polyurethane films and foams.

A particularly preferred class of polyhydric compounds is polysaccharides having a molecular weight of at least about 3000. Included are polysaccharides containing repeating units of a single monosaccharide (homoglycans) or mixtured monosaccharide units (heteroglycans), for example L-fructose, xylan, D-xylose (mono) and tragacanth, D-xylose and D-galacturonic acid (hetero), The polysaccharides can contain substituents such as amino sugar units, pentose sugar units, uronic sugar units, sugar groups containing ethers and the like. The polysaccharides can be linear or branched, although branched polysaccharides, which constitute a preferred class herein, exhibit better solubility and are less likely to undergo retrogradation than the linear polysaccharides. The type of glycosidic linkage does not appear to be critical though generally the 1-4 and 1-6 linkages are usually employed because of their abundance.

Some examples of useful polysaccharides are xylan, amylopectins, amylose, fructans, fucan, floridean starch, glycogens, starches, levans, dextrans, capreolan yeast glucan and gums and mucilages such as carob, tragacanth, locust bean, guaran, cashew, lemon, karaya, ghatti, cholla, arabic and damson. A preferred group of polysaccharides is selected from the group consisting of potato starch, corn starch, tapioca starch, arrowroot starch, gum arabic, gum tragacanth and dextran.

The high molecular weight polyhydric organic compound is typically present in the metal ion solution in the range of about 0.1 to 11 percent by weight based on the weight of metal in the metal component, or more usually 1 to 4 percent by weight based on the weight of metal in the metal component.

Soluble metal salts are known for essentially all metals. In specific regard to the metal components of the present invention the following soluble metal compounds are illustrative: titanium trichloride, vanadium diiodide, chromium (III) nitrate, manganese (II) titanate, iron (III) nitrate, cobalt (II) acetate, nickel nitrate, copper nitrate, niobium potassium fluoride, molybdenum dioxydichloride, ruthenium tetrachloride, rhodium dioxide, palladium chloride, stannous chloride, antimony trichloride, tungsten dioxydichloride, rhenium trichloride, osmium trichloride, iridium tribromide, platinum tetrachloride, gold chloride, mercuric nitrate, thallium acetate, lead fluorosilicate, bismuth dioxide, polonium tetrachloride, magnesium selenate, aluminum bromate, calcium chlorate, scandium chloride, zinc sulfate, strontium tetrasulfide, cadmium sulfate, barium trisulfide, beryllium bromide, lanthanum heptahydrate chloride, cesium carbonate, germanium tetrafluoride, europium iodide, gallium nitrate, selenium oxide, idium trichloride and the like.

In addition to compounds of the type listed above, less soluble compounds can be employed in conjunction with other materials and techniques which will increase their solubility. For example, many insoluble or poorly soluble compounds, e.g., $Fe_2O_3$ and $ZnO$ are soluble in hot concentrated acids. The addition of a cooled solution thereof to an alkaline solution will result in the precipitation of the insoluble hydroxide. Such techniques and manipulations are well known in the art and their application in the operation of the process of the present invention is contemplated.

In addition to the metals the catalyst often contain various non-metallic components which also serve as promoters, initiators, stabilizers or the like. Alkali metal compounds are frequently present in the oxidative dehydrogentation catalyst in limited quantities such as $Li_2O$, $Na_2O$ and $K_2O$. Other additives are sulfur, phosphorus, silicon, boron or mixtures thereof, for example, sulfates, sulfites, sulfides, alkylmercaptains, sulfuric acid, phosphates, phosphoric acid, silica, silicates, boron trifluorides and the like. such additives are disclosed in U.S. Pat. Nos. 3,247,278; 3,270,080; 3,303,238; 3,324,195; 3,398,100.

Halogen is also often present in oxidative dehydrogenations to improve the results. The presence of halogen in the dehydrogenation zone is particularly effective when the compound to be dehydrogenated is saturated, such as a saturated hydrocarbon. The halogen present in the dehydrogenation zone may be either elemental halogen or any compound of halogen which would liberate halogen under the conditions of reaction. Suitable sources are such as hydrogen iodide, hydrogen bromide and hydrogen chloride, ethyl iodide, methyl bromide, methyl chloride, 1,2-dibromoethane, ammonium iodide, ammonium bromide, ammonium chloride, sulfuryl chloride, etc. The halogen may be liberated partially or entirely by a solid source as shown in U.S. Pat. 3,130,241. Mixture of halogens and halogen sources can be used. The amount of halogen, calculated as elemental halogen, may be as little as about 0.0001 or less mole of halogen per mole of organic compound to be dehydrogenated to as high as 0.2 or 0.5. The use of halogens in oxidative dehydrogenations is shown in U.S. Pat. Nos. 3,210,436; 3,207,805, 3,207,810; 3,277,207; 3,278,626; 3,308,182-3; 3,308,200; 3,316,320; 3,356,750; 3,359,343; 3,374,283; 3,382,290; 3,440,298; 3,442,968.

The catalysts may have the iron combined in crystalline structure with oxygen and zinc and one or more other metallic elements, as mentioned above. For example, a preferred type of ferrite is that essentially or approximately of the formula, $MeFe_2O_4$, where Me represents zinc alone or with another divalent metal ion with an ionic radius approximately between 0.5 and 1.1 A., preferably between about 0.6 and 1.0 A. Me may be, e.g., zinc and one of the divalent ions as Mg, Ca, Sr, Ba, Cr, Mn, Co, Ni or Cd to form a ferrite such as $Zn_{0.5}Mg_{0.5}Fe_2O_4$ or $Zn_{0.25}Mg_{0.75}Fe_2O_4$. Moreover, the symbol Me may represent a combination of zinc ion with other metal ions which have an average valence of two.

Suitable catalysts may also be zinc ferrites wherein other metals are partially substituted for the iron. For example, atoms having a valence of +3 may be partially substituted for some of the $Fe^{+++}$ atoms. Also, metal atoms having a valence of +4 may replace some of the $Fe^{+++}$ ions. However, the catalysts will still suitably have iron present in an amount described above in relation to the total atoms of the second metallic ingredients. Some ferrites are described in Ferromagnetism, by Richard M. Bozorth (D. Van Nostrand Co., Inc., 1951) which disclosure is hereby incorporated by reference.

The preferred compositions exhibit a certain type of X-ray diffraction pattern. The preferred compositions do not have any sharp X-ray diffraction reflection peaks as would be found, e.g., in a highly crystalline material having the same chemical composition. Instead, the ferrite composition of this invention exhibit reflection peaks which are relatively broad. The degree of sharpness of the reflection peak may be measured by the reflection peak band width at half height (W h/2). In other words, the width of the reflection peak as measured at one-half of the distance to the top of the peak is the "band width at half height". The band width at half height is measured in units of °2 theta. Techniques for measuring the band widths are discussed, e.g. in Chapter 9 of Klug and Alexander, X-ray Diffraction Procedures, John Wiley and Son, N.Y., 1954. Suitable preferred ferrites according to this invention are zinc ferrites having X-ray diffraction peaks within the d-spacings 4.83 to 4.89, 2.95 to 3.01, 2.51 to 2.57, 2.40 to 2.46, 2.08 to 2.14, 1.69 to 1.75, 1.59 to 1.65 and 1.46 to 1.52 with the most intense peak being between 2.51 to 2.57.

Ferrite formation may be accomplished by reacting an active compound of iron with an active compound of zinc. The hydroxide precipitates of the present invention are suitable active compounds. During the formation of the ferrites such hydroxides are converted to oxides.

The catalysts may contain an excess of iron over the stoichiometric amount to form the ferrite. for example, in a ferrite of the type $MeFe_2O_4$ the stoichiometric amount of iron would be 2 atoms per atom of Me. The iron (calculated as $Fe_2O_3$) may be present in an amount of at least about 10 percent in excess of the stoichiometric amount and preferably may be present in an amount of at least 14 percent in excess. Suitable ranges of iron are from about 10 to 200 percent excess. Similarly the catalysts may contain an excess of the Me over the stoichiometric amount required.

The precipitating agent is a solution of lithium hydroxide, sodium hydroxide, potassium hydroxide, rubidium hydroxide, cesium hydroxide or a mixture of any of these hydroxides at a normality of between 2 and 4, preferably about 2.5 to 3.5. the normality of the alkali metal hydroxide solution is a very essential feature of the process of preparing the zinc ferrite catalyst. The precipitate obtained using a 2N solution was found to be highly gelatinous. This material was extremely difficult to handle during the purification. At 4N alkali metal hydroxide concentration the catalyst has good physical appearance, however, removal of residual alkali was found to be extremely difficult. The degree of water washing was prohibitive.

The precipitate prepared at 3N alkali metal hydroxide concentration is a more granular precipitate which is easily washed free of residual hydroxide and unreacted starting materials and easily recovered in a readily handled form. Preparation of the ferrite precursor at 3N alkali metal hydroxide concentration required a relatively short period of time and was easily reproducible.

The catalyst preparations are generally carried out at atmospheric pressure, although either sub or super atmospheric pressures, for example 0.5 to 50 atmospheres can be employed if the conditions warrant. Temperature of the catalyst precipitation are relatively mild being at approximately room temperature (about 25° C.). Temperatures lower than room can be employed so long as the reactants are sufficiently soluble, generally temperatures no lower than 20° C. will be employed. Higher temperatures can be employed to improve the solubility of the reactants, but generally there is no need to exceed about 100° C. At higher temperatures, i.e. 30°–50° C. or higher, the viscosity effect obtained from the high molecular weight polyhydric compound is decreased.

The solutions containing the zinc ion and the precipitation agent can be contacted in any of the ways previously employed for precipitation known and used in the prior art. The two solutions can be mixed together with mild or vigorous agitation depending on the size of particles desired. The metal ion containing solution is conveniently sprayed into a solution of the precipitating agent in the form of droplets or a steady stream. The droplets produce spheres of catalyst and the steady stream a cylindrical type catalyst. The catalysts prepared according to this invention have been found to have excellent reactivity in oxidative dehydrogenations and superior strength. The catalysts of this invention are suitable for both fixed and moving bed operations, such as a fluidized bed.

In the preparation of the catalysts the high molecular weight polyhydric organic compound is added to the solution of zinc ions (any other metal ions would also be in this solution). Generally if the ionic zinc solution were prepared by heating, the solution is cooled prior to adding the polyhydric compound, usually to 100° C. or less, preferably to 50° C. or less. The precipitate which is obtained is a granular gelatinous material that is easily filtered. The recovered filtrate is washed and dried.

Zinc ferrites may be obtained by conducting the reaction to form the ferrites at relatively low temperatures, that is, at temperatures lower than some of the very high temperatures used for the formation of ferrites prepared for semiconductor application. The very intimate relationship of the zinc and iron reactants obtained by the co-precipitation of the present invention facilitates the reaction. Generally the temperature of reaction for the formation of zinc ferrites will be less than 1300° C. and preferably less than 1150° C. Preferably the ferrites are formed at 400°–1100° C. in a controlled atmosphere, e.g. air, nitrogen, helium, a reducing atmosphere such as hydrogen, carbon monoxide and the like. The reaction time at the elevated temperature in the formation of the zinc ferrite catalyst may run from 5 minutes to 4 hours. Some improvement in the catalytic activity of zinc ferrites may be obtained by reducing the catalyst. The reduction may be accomplished prior to the initial dehydrogenation, or after the catalyst has been used. The reduction may be accomplished with any effective reducing gas which is capable of reducing iron to a lower valence such as hydrogen, carbon monoxide, or hydrocarbons. The temperature of reduction can be from 200° to 900° C. or higher.

The preparation of catalysts is often described as an art. Experienced researchers and chemists often have difficulty reproducing a particular catalyst. This defect is even more often encountered in commercial production of catalysts. The gel precipitation method of the present invention adds the intangible but extremely valuable asset of giving an easily handled catalyst preparation method for preparing catalysts having consistent properties.

The catalysts of this invention can be applied to the dehydrogenation of a wide variety of organic compounds. Such compounds normally will contain from 2 to 20 carbon atoms, at least one

grouping, having a boiling point below about 350° C., and may contain other elements, in addition to carbon and hydrogen such as oxygen, halogens, nitrogen and sulfur. Preferred are compounds having 2 to 12 carbon atoms, and especially preferred are compounds of 3 to 6 or 8 carbon atoms. A particularly preferred grouping has 4 to 8 carbon atoms and is desirably hydrocarbon compounds.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustration of dehydrogenations include propionitrile to acrylonitrile; propionaldehyde to acrolein; ethyl chloride to vinyl chloride; methyl isobutyrate to methyl methacrylate; 2 or 3 chlorobutene-1 or 2, 3 dichlorobutane to chloroprene; ethyl pyridine to vinyl pyridine; ethylbenzene to styrene; isopropylbenzene to α-methyl styrene; ethylchlorohexane to styrene; cyclohexane to benzene; ethane to ethylene to acetylene; propane to propylene or methyl acetylene, allene, or benzene; isobutane to isobutylene n-butane to butene and butadiene-1,3; n-butene to butadiene-1,3 and vinyl acetylene; methyl butene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentane to xylenes; and the like. This invention may be useful for the formation of new carbon to carbon bonds by the removal of hydrogen atoms such as the formation of a carbocyclic compound from two aliphatic hydrocarbon compounds or the formation of a dicyclic compound from a monocyclic compound having an acyclic group such as the conversion of propene to diallyl. Representative materials which are dehydrogenated by the novel process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3 dichlorobutane, 1,4 dichlorobutane, the chlorofluoroethanes, methyl pentane, methylethyl ketone, diethyl ketone, n-butyl alcohol, methyl propionate, and the like.

Suitable dehydrogenation reactions are the following: acyclic compounds having 4 to 5 non-quaternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene to cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

The preferred compounds to be dehydrogenated are hydrocarbons with a particular preferred class being acyclic non-quaternary hydrocarbons having 4 to 5 contiguous carbon atoms or ethyl benzene and the preferred butene, 3-methyl-1-butene, 3-methyl-2-butene, isoprene, styrene or mixtures thereof. Especially preferred as feed are n-butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about or in exccess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

The organic compounds to be dehydrogenated is contacted with oxygen in order for the oxygen to oxidatively dehydrogenate the compound. Oxygen may be fed to the reactor as pure oxygen, as air, as oxygen-enriched air, oxygen mixed with diluents, and so forth. Oxygen may also be added in increments to the dehydrogenation zone. Although determinations regarding the mechanism of reaction are difficult, the process of an oxidative dehydrogenation process is one wherein the predominant mechanism is by the reaction of oxygen with the hydrogen released from the hydrocarbon.

The amount of oxygen employed may vary depending upon the desired result such as conversion, selectivity and the number of hydrogen atoms being removed. Thus, to dehydrogenate butane to butene requires less oxygen than if the reaction proceeds to produce butadiene. Normally oxygen will be supplied (including all sources, e.g. air to the reacotr) in the dehydrogenation zone in an amount form about 0.2 to 1.5, preferably 0.3 to 1.2, mols per mol of $H_2$ being liberated from the organic compound. Ordinarily the mols of oxygen supplied will be in the range of from 0.2 to 2.0 mols per mol of organic compound to be dehydrogenated and for most dehydrogenations this will be within the range of 0.25 to 1.5 mols of oxygen per mol of organic compound. Among the advantages noted are that the instant catalysts will allow higher ratios of oxygen to hydrocarbon than catalyst prepared conventionally. Higher oxygen to hydrocarbon ratios generally provide higher conversions with a corresponding decrease in selectivity, however, the catalysts of the present invention do not exhibit as rapid a decrease in selectivity as the analogous conventionally prepared catalyst thus providing higher yields than were possible previously.

Frequently the reaction mixture contains a quantity of steam or diluent such as nitrogen with the range generally being between about 2 and 40 mols of steam per mol of organic compound to be dehydrogenated. Preferably, steam will be present in an amount from about 3 to 35 mols per mol of organic compound to be dehydrogenated and excellent results have been obtained within the range of about 5 to about 30 mols of steam per mol of organic compound to be dehydrogenated. The functions of the steam are several-fold, and the steam may not merely act as a diluent. Diluents generally may be used in the same quantities as specified for the steam. These gases serve also to reduce the partial pressure of the organic compound.

The temperature for the dehydrogenation reaction generally will be at least about 250° C., such as greater than about 300° C. or 375° C., and the maximum temperature in the reactor may be about 700° C. or 800° C. or perhaps higher such as 900° C. under certain circumstances. However, excellent results are obtained within the range of or about 350° C. to 700° C., such as from or about 400° C. to or about 675° C. The temperatures are measured at the maximum temperature in the dehydrogenation zone.

The gaseous reactants may be conducted through the reaction chamber at a fairly wide range of flow rates. The optimum flow rates will be dependent upon such variables as the temperature of reaction, pressure, particle size, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing catalyst is that original void volume of reactor space containing catalyst.

The following examples will further illustrate the invention as described above. Percentages are by weight unless otherwise specified. Results are given in mol %. The presence of the $ZnFe_2O_4$ was established by X-ray analysis as previously described. The produce analysis was by gas liquid chromatography.

EXAMPLE 1

Catalyst Preparation

The following reagents were used

| | | |
|---|---|---|
| $ZnCl_2$ | 169.8 grams | |
| $FeCl_3 \cdot 6H_2O$ | 672.0 grams | |
| dextran (200,000–300,000) (molecular weight) | 6.0 grams | (2% based on $ZnFe_2O_4$) |
| 3 N.NaOH | 6.0 liters | | the $ZnCl_2$ and $FeCl_3 \cdot 6H_2O$ were added to 1 liter of demineralized water and the mixture heated until solution was obtained. The dextran was dissolved in a small amount of demineralized water then added to the $ZnCl_2/FeCl_3 \cdot 6H_2O$ solution. This mixture was stirred for 15 minutes and cooled in an ice bath. The cooled solution was sprayed into a 3N solution of NaOH through a 26 gauge needle which was moved in a circular motion over the NaOH solution. The precipitate was aged for 40 minutes, filtered under vacuum and washed thoroughly with water until the wash water indicated pH 6. The precipitate was then dried in an oven for about 16 hours at about 160° C. under nitrogen. The dried precipitate was loaded into a 1 inch stainless steel reactor and calcined at 350° C. for 2 hours under a flow of nitrogen.

a total of 140 grams of the calcined catalyst was dry ball milled for 12 hours. A supported catalyst containing 40% actives was prepared using the following materials:

| | |
|---|---|
| Alumina (AMC*) | 140 grams |
| $ZnFe_2O_4$ | 94.3 grams |
| $H_3PO_4$ | 40.7 ml of 0.07167 g/ml $H_3PO_4$ (3 wt. % $H_3PO_4$ based on $ZnFe_2O_4$) |

*3 to 5 mesh, surface area 1 mm/gram

The 40.7 ml of $H_3PO_4$ was further diluted to a total of 150 ml solution. The $ZnFe_2O_4$ was then added followed by the AMC support. The mixture was then dried in a tumbling machine.

EXAMPLE 2

The finished catalyst from Example 1 was loaded into a 1 inch diameter IPS stainless steel vertical reactor in a 125 cc bed. The catalyst was reduced by hydrogen for 1½ hours at 700° F (400 cc/min). The hydrogen was terminated and steam and nitrogen introduced as the reactor was cooled to reaction temperature. The nitrogen was terminated and a feed of n-butenes for conversion to butadiene LHSV of 1.5 started. The results are in mole %. The conditions and results are in Table 1.

Table 1

| | Conditions | | | Results |
|---|---|---|---|---|
| Total hours on stream | Temp. inlet °F | max | Steam/$O_2$/Butenes mol ratio | Conversion/Selectivity/Yield mol % |
| 20 | 610 | 830 | 20/0.550/1 | 61/93/57 |
| 420 | 610 | 880 | 18/0.717/1 | 70/93/65 |
| 1000 | 650 | 750 | 17/0.717/1 | 75/93/70 |

The catalyst showed no loss of activity at 1000 hours at very high yields.

EXAMPLE 3

The catalyst was prepared as in Example 1 but was calcined at 450 C. for 2 hours under nitrogen then loaded in the reactor and reduced for 1½ hours at 750° F. with hydrogen. An n-butene feed was introduced at 1.5 LHSV. The other conditions and results are in Table II.

Table II

| Total Hours on Stream | Conditions Temp. inlet °F. | max | Steam/O₂/Butenes mol ratio | Results Conversion/Selectivity/Yield mol % |
|---|---|---|---|---|
| 300 | 600 | 850 | 20/0.550/1 | 70/95/67 |
| 301 | 620 | 860 | 18/0.550/1 | 72/95/68 |
| 801 | 630 | 900 | 18/0.717/1 | 78/94/73 |
| 1001 | 670 | 940 | 17/0.717/1 | 78/94/73 |

In this Example and in Example 2 it should be noted that the large increase in conversion did not result in the expected loss of selectivity.

EXAMPLE 4

The procedure of Example 1 was followed with 3N KOH being used instead of NaOH. The precipitate was dried at 120° C. under $N_2$ and calcined at 450° C. for 2 hours under nitrogen and dry ball milled for 30 hours and deposited on alumina as described. The catalyst was loaded into the 1 inch stainless steel reactor and reduced for 1½ hours at 750° F. with hydrogen. An n-butene feed at LHSV 1.5 was converted to butadiene. The results and conditions are in Table III.

Table III

| Total Hours on Stream | Conditions Temp. inlet °F | max | Steam/O₂/Butenes mol ratio | Results Conversion/Selectivity/Yield mol % |
|---|---|---|---|---|
| 20 | 640 | 840 | 20/.55/1 | 61/93.7/57.2 |
| 4 | 645 | 840 | 18/.55/1 | 60.1/93.8/56.4 |

EXAMPLES 5 AND 6

In these examples 2N and 4N NaOH was employed respectively. No catalyst was prepared in each case.
2N NaOH It was found that the precipitate was so gelatinous that the filter paper was plugged. The filter was extremely slow and washing of the filtrate impossible within reasonable period of time. After 8 hours of filtration, the washing had not really begun and further efforts were abandoned.
4N NaOH This material filtered easily, however, after 16 hours of washing a pH of 6 had not been achieved and the effort was abandoned.

EXAMPLE 7

This example presents a Zn ferrite prepared by a conventional slurry technique and shows the result of its use for the dehydrogenation of n-butenes.

Reactants

| | |
|---|---|
| $Fe_2O_3$ (87%) | 9144.6 grams |
| ZnO (99.7%) | 3628.8 grams |
| $ZnCl_2$ | 68.0 grams |
| Weight ratio of $Fe_2O_3$/ZnO = 2.2/1 | |

To the above solids 37 liters of water was added and slurried for 3½ hours then dried for 16 hours at 260° F.

The dried cake was granulated and blended with water and calcined at 1200° F. for 13.95 minutes by passage through an inclined calcination tube with a flow of nitrogen of 0.65 ft.²/minute counter to the direction of catalyst flow.

The same reactor as described in Example 1 was used for the runs reported in Table IV. The conditions and results are shown in Table IV. Fresh catalyst was used for each run.

Table IV

| Run | Reduction (hrs) Hydrogen 400 cc/min | Stream | O₂/Stm/HC mol ratio | C/S/Y mol % | $T_i$ (°F.) | $T_{max}$ (°F.) |
|---|---|---|---|---|---|---|
| 1 | 1½ at 1050°F | — | — | — | — | — |
| | | 48 | .55/17/1 | 61.4/91.2/56.0 | 677 | 951 |
| | | 112¾ | .55/17/1 | 62.6/93.2/58.3 | 676 | 916 |
| | | 138 | .55/17/1 | 49.6/90.9/45.1 | 666 | 938 |
| | | 143¼ | .55/17/1 | 48.5/91.4/44.3 | 668 | 929 |
| 2 | 1 at 1050°F | — | — | — | — | — |
| | | 20¾ | .55/20/1 | 59.8/92.5/55.3 | 629 | 924 |
| | | 70¼ | .55/20/1 | 59.4/92.8/55.1 | 650 | 910 |
| | | 73¾ | .55/17/1 | 61.6/92.1/56.7 | 648 | 932 |
| | | 77¼ | .55/17/1 | 61.9/92.3/57.1 | 649 | 931 |
| | | 142½ | .55/17/1 | 53.4/93.2/49.8 | 649 | 913 |
| | | 172 | .55/17/1 | 49.7/90.7/45.1 | 640 | 936 |
| 3 | 1½ at 950°F. | — | — | — | — | — |
| | | 19¼ | .55/20/1 | 56.8/92.4/52.5 | 650 | 910 |
| | | 69¼ | .55/20/1 | 55.1/93.0/51.2 | 648 | 877 |
| | | 93¼ | .55/20/1 | 55.2/93.7/51.7 | 646 | 912 |
| | | 95½ | .55/17/1 | 57.1/92.1/52.6 | 636 | 915 |
| | | 164¼ | .55/17/1 | 52.8/93.2/49.2 | 620 | 930 |

Table IV-continued

| Run | Reduction (hrs) Hydrogen 400 cc/min | Stream | O₂/Stm/HC mol ratio | C/S/Y mol % | $T_i$ (°F.) | $T_{max}$ (°F.) |
| --- | --- | --- | --- | --- | --- | --- |
| | | 181½ | .55/17/1 | 55.4/93.0/51.5 | 633 | 945 |
| | | 422 | .55/17/1 | 45.5/93.2/42.4 | 636 | 900 |

As can be seen from the Table there is a rapid and substantial decline in both conversion and selectivity with use.

The invention claimed is:

1. In a process for the oxidative dehydrogenation of organic compounds having at least two adjacent, hydrogen containing carbon atoms in the presence of a catalyst wherein the improvement comprises utilizing a zinc ferrite catalyst prepared by the steps of (a) contacting a solution of a soluble metal component comprising zinc and iron with a precipitating agent to precipitate an insoluble metal component comprising zinc and iron, said solution containing in addition to the soluble metal component from 0.1 to 11 weight percent of a soluble polyhydric organic compound based on the weight of metal and (b) calcining the precipitate to form said zinc ferrite oxidative dehydrogenation catalyst, wherein the precipitating agent is a solution of a hydroxide of a metal selected from the group consisting of Li, Na, K, Rb, and Cs, said precipitating solution having a normality of between 2 and 4 and said polyhydric compound contains at least 2 hydroxyl groups and is selected from the group consisting of organic alcohols, polyesters, polyethers, polysaccharides and mixtures thereof having a molecular weight of at least about 3,000.

2. The process according to claim 1 wherein the soluble polyhydric compound is selected from the group consisting of (a) polyesters derived from polybasic acids and polyols wherein the polybasic acids are adipic acid, succinic acid, sebacatic acid and azelaic acid and the polyols are pentaerythritol, xylitol and sorbitol, (b) polyethers being the condensation of ethylene oxide, propylene oxide and mixtures thereof with glycerol, pentaerythritol, xylitol, sorbitol and polysaccharides and (c) polysaccharides containing repeating units of a single monosaccharide or mixed monosaccharide units.

3. The process according to claim 1 wherein the molecular weight of the polyhydric compound is between about 4000 and 400,000.

4. The process according to claim 3 wherein the polyhydric compound has at least three hydroxyl groups per molecule.

5. The process according to claim 3 wherein the polyhydric compound is a polyester or polyether.

6. The process according to claim 4 wherein the polyhydric compound is a polysaccharide.

7. The process according to claim 6 wherein the polysaccharide is branched.

8. The process according to claim 7 wherein the polysaccharide has 1-4, 1-6 or mixed glycoside linkage.

9. The process according to claim 7 wherein the polysaccharide is dextran.

10. The process according to claim 2 wherein the polyhydric compound is a polysaccharide selected from the group consist of xylan, amylopectins, amylose, fructans, fucan, floridean starch, glycogens, levans, dextrans, capreolan yeast glucan, potato starch, corn starch, tapioca starch, arrowroot starch, gum arabic and gum tragacanth.

11. The process according to claim 1 wherein there is 0.1 to 4 weight percent of polyhydric compound.

12. The process according to claim 1 wherein the solution of soluble metal component and the precipitating agent are contacted with agitation.

13. The process according to claim 1 wherein the solution of soluble metal component is sprayed into the precipitating agent.

14. The process according to claim 1 wherein said organic compounds have 4 to 8 carbon atoms.

15. The process according to claim 14 wherein the organic compounds are hydrocarbons.

16. The process according to claim 15 wherein said hydrocarbons are acyclic non-quaternary compounds having 4 to 5 contiguous carbon atoms or ethyl benzene.

17. The process according to claim 16 where the hydrocarbons are n-butenes.

18. The process according to claim 9 wherein the organic compounds are n-butenes.

* * * * *

UNITED STATES PATENT OFFICE
CERTIFICATE OF CORRECTION

PATENT NO. : 3,937,748

DATED : February 10, 1976

INVENTOR(S) : Edward J. Miklas

It is certified that error appears in the above-identified patent and that said Letters Patent are hereby corrected as shown below:

Title reads "OXIDATIVE DEHYDROGENATION USING GEL PRECIPITATED CATALYST PREPARATION" for should read -- OXIDATIVE DEHYDROGENATION USING GEL PRECIPITATED CATALYST --.

Under Heading "References Cited", "Bavars et al" should read -- Bajars et al --.

On cover sheet, Attorney, Agent, or Firm reads "Elton N. Dry..." but should read -- N. Elton Dry ... --.

Col. 1, line 43 reads "$Mg^{--}Ni^{--}$ or $Zn^{--}$" but should read -- $Mg^{++}Ni^{++}$ or $Zn^{++}$ --.

Col. 1, line 45 reads "hexaggonal" but should read -- hexagonal --.

Col. 3, line 40 reads "(hetero)," but should read -- (hetero). --.

Col. 5, line 53 reads ". for example," but should read -- . For example, --.

Col. 5, line 67 reads ". the normality..." but should read -- . The normality... --.

Col. 8, line 39 reads "exccess of" but should read -- excess of --.

Col. 8, line 63 reads "to the reacotr" but should read -- to the reactor --.

Col. 10, line 12 reads "the $ZnCl_2$" but should read -- The $ZnCl_2$ --.

UNITED STATES PATENT OFFICE
CERTIFICATE OF CORRECTION

PATENT NO. : 3,937,748
DATED : February 10, 1976
INVENTOR(S) : Edward J. Miklas

It is certified that error appears in the above—identified patent and that said Letters Patent are hereby corrected as shown below:

Col. 10, line 28 reads "a total of" but should read -- A total of --.

Col. 10, line 39 reads "*3 to 5 mesh, surface area 1 mm/gram" but should read -- *3 to 5 mesh, surface area $\leq$ 1 mm/gram --.

Signed and Sealed this

Twenty-first Day of September 1976

[SEAL]

Attest:

RUTH C. MASON
*Attesting Officer*

C. MARSHALL DANN
*Commissioner of Patents and Trademarks*